(12) United States Patent
Parnas et al.

(10) Patent No.: US 10,086,339 B2
(45) Date of Patent: Oct. 2, 2018

(54) POLYMERS AND MEMBRANES FOR SEPARATION OF POLAR ORGANIC COMPOUNDS FROM AQUEOUS MIXTURES AND METHODS OF USING (71) Applicant: THE UNIVERSITY OF CONNECTICUT, Farmington, CT (US)

(72) Inventors: Richard Steven Parnas, Ashford, CT (US); Alexandru Asandei, Vernon, CT (US); Baishali Kanjilal, West Haven, CT (US); Iman Noshadi, Cambridge, MA (US)

(73) Assignee: THE UNIVERSITY OF CONNECTICUT, Farmington, CT (US)

( * ) Notice: Subject to any disclaimer, the term of this patent is extended or adjusted under 35 U.S.C. 154(b) by 139 days.

(21) Appl. No.: 15/066,697

(22) Filed: Mar. 10, 2016

(65) Prior Publication Data
US 2016/0264692 A1 Sep. 15, 2016

Related U.S. Application Data (60) Provisional application No. 62/130,974, filed on Mar. 10, 2015, provisional application No. 62/139,194, filed on Mar. 27, 2015.

(51) Int. Cl.
B01D 71/82 (2006.01)
B01D 69/02 (2006.01)
C08G 77/16 (2006.01)
B01D 61/36 (2006.01)
B01D 71/00 (2006.01)
C08G 77/388 (2006.01)
(Continued)

(52) U.S. Cl.
CPC ............ B01D 71/82 (2013.01); B01D 69/02 (2013.01); B01D 71/40 (2013.01); B01D 71/48 (2013.01); B01D 71/60 (2013.01); C07C 29/76 (2013.01); C08F 26/06 (2013.01); C08G 77/388 (2013.01); C09D 183/08 (2013.01); B01D 61/362 (2013.01); B01D 2323/04 (2013.01); B01D 2325/38 (2013.01); C08G 77/16 (2013.01)

(58) Field of Classification Search
None
See application file for complete search history.

(56) References Cited

U.S. PATENT DOCUMENTS 6,361,983 B1 3/2002 Ames
6,428,992 B1 8/2002 Roturier et al.
(Continued)

FOREIGN PATENT DOCUMENTS

WO 2004101479 A2 11/2004

OTHER PUBLICATIONS

Anand et al; "A novel downstream process for 1,3-propanediol from glycerol-based fermentation"; Appl Microbiol Biotechnol; vol. 90; 2011; pp. 1267-1276.
(Continued)

Primary Examiner — Krishnan S Menon
(74) Attorney, Agent, or Firm — Cantor Colburn LLP (57) ABSTRACT A polymer having a contact angle with water that is greater than or equal to 90° and a contact angle with 1,3-propane diol that is less than 90°. A pervaporation membrane comprising the polymer and a process for purifying a fermentation broth using a pervaporation membrane comprising the polymer is also described.

17 Claims, 7 Drawing Sheets (51) Int. Cl.

| | |
|---|---|
| C07C 29/76 | (2006.01) |
| B01D 71/60 | (2006.01) |
| B01D 71/48 | (2006.01) |
| C08F 26/06 | (2006.01) |
| B01D 71/40 | (2006.01) |
| C09D 183/08 | (2006.01) |

(56) References Cited

U.S. PATENT DOCUMENTS

| | | |
|---|---|---|
| 6,479,716 B2 | 11/2002 | Hilaly et al. |
| 7,056,439 B2 | 6/2006 | Baniel et al. |

OTHER PUBLICATIONS

Cho et al; "A novel separation and purification process for 1,3-propanediol"; Process Biochemistry; vol. 41; 2006; pp. 739-744.

Gong et al.; "The possibility of the desalination of actual 1,3-propanediol fermentation broth by electrodialysis"; Desalination; vol. 161; 2004; pp. 169-178.

Hao et al; "Downstream processing of 1,3-propanediol fermentation broth"; Journal of Chemical Technology and Biotechnology; vol. 81; 2006; pp. 102-108.

Izak et al; "Stability and selectivity of a multiphase membrane, consisting of dimethylpolysiloxane on an ionic liquid, used in the separation of solutes from aqueous mixtures by pervaporation"; Green Chemistry; vol. 8; 2006; pp. 947-948.

Li et al; "Aqueous two-phase extraction of 1,3-propanediol from glycerol-based fermentation broths"; Separation and Purification Technology; vol. 66; 2009; pp. 472-478.

Li et al; "Separation of 1,3-Propanediol from Aqueous Solutions Using Pervaporation through an X-type Zeolite Membrane"; Ind. Eng. Chem. Res.; vol. 40; 2001; pp. 1952-1959.

Li et al; "Separation of 1,3-propanediol from glycerol and glucose using a ZSM-5 zeolite membrane"; Journal of Membrane Science; vol. 191; 2001; pp. 53-59.

Malinowski; "Reactive Extraction for Downstream Separation of 1,3-Propanediol"; Biotechnology Progress; vol. 16; 2000; pp. 76-79.

Saxena et al; "Microbial production of 1,3-propanediol: Recent developments and emerging opportunities"; Biotechnology Advances; vol. 27; 2009; pp. 895-913.

Xiu et al; "Present state and perspective of downstream processing of biologically produced 1,3-propanediol and 2,3-butanediol"; Appl Microbiol Biotechnol; vol. 78; 2008; pp. 917-926.

Zeng et al.; "Bulk Chemicals from Biotechnology: The Case of 1,3-Propanediol Production and the New Trends"; Advances in Biochemical Engineering/Biotechnology; vol. 74; 2002; pp. 239-259.

Kanjilal et al; "Functionalised Siloxane membranes for pervaporative purification of 1,3 propanediol from fermentation broths: Polymer synthesis, characterization, membrane fabrication & application"; Presentation Slides; 2013; 29 pages.

Kanjilal et al; "Imidazolium Dibutylphosphate Ionic Liquid Based Mathacrylate Polymer Membranes for Efficient Pervaporative Enrichment of 1,3-propanediol From Binary Aqueous Mixtures"; The Royal Society of Chemistry; 2013; 19 pages.

POLYMERS AND MEMBRANES FOR SEPARATION OF POLAR ORGANIC COMPOUNDS FROM AQUEOUS MIXTURES AND METHODS OF USING

CROSS REFERENCE TO RELATED APPLICATIONS

This application claims the benefit of U.S. Provisional Application No. 62/130,974 filed on Mar. 10, 2015 and U.S. Provisional Application No. 62/139,194 filed on Mar. 27, 2015, both of which are incorporated by reference herein in their entirety.

FEDERAL RESEARCH STATEMENT

This invention was made with government support under Grant #DE-EE000311.6 awarded by the U.S. Department of Energy. The government has certain rights in the invention.

BACKGROUND

Glycerol, a platform chemical for the production of intermediate biorenewable chemicals, can be obtained as a low value byproduct from a variety of industries such as the production of biodiesel. The fermentative conversion of glycerol to intermediate biorenewable chemicals such as 1,3-propanediol (1,3-PD) is an environmentally sustainable use of the oversupply. However, the principal impediment in fermentative conversion of glycerol to 1,3-PD lies in the downstream purification of the 1,3-PD given that it has to be enriched from low starting concentrations. The separation of 1,3-PD from the fermentation broth can account for more than 50% of the total production cost. The hydrophilicity of 1,3-PD compounds the complexity of purification. Conventional processes like distillation, chromatography, and reactive extraction amongst others have been used, but are associated with high energy usage, low yield, and/or process complication issues. For example, the high hydrophilicity of 1,3-PD has been the major impediment in using a method as simple as solvent extraction.

BRIEF DESCRIPTION

Polymers are disclosed to separate polar organic molecules from aqueous mixtures. These polymers may also separate polar organic molecules from aqueous mixtures and from other polar organic molecules in the aqueous mixture. The polar organic molecule may be 1,3-propanediol and the aqueous mixture may be a fermentation broth containing many compounds, typically water, ethanol or other organic alcohol, organic acids such as acetic acid and butyric acid, and in some cases glycerin.

Disclosed herein are polymers having a contact angle with water that is greater than or equal to 90° and a contact angle with 1,3-propane diol that is less than 90°. The polymers can be used in a pervaporation membrane for the separation of 1,3-propane diol from an aqueous mixture, more specifically a fermentation broth. Methods of separation are described herein.

Also disclosed herein is a polymer having a contact angle with water that is greater than or equal to 90° and a contact angle with an organic molecule that is less than 90° wherein the organic molecule comprises one or more polar functional groups. The polymer can be used in a pervaporation membrane for the separation of the organic molecule from an aqueous mixture.

The above described and other features are exemplified by the following figures and detailed description.

BRIEF DESCRIPTION OF THE DRAWINGS

FIGS. 1-10 are graphical representations of data from the Examples.

DETAILED DESCRIPTION

Pervaporation mitigates the challenge of high energy associated with processes involving phase change. Pervaporation uses membranes with affinities tailored to be selective towards a given component. A minor component can be more selectively isolated, hence reducing the bulk energy usage.

In the case of polar organic molecules in aqueous solutions the creation of a pervaporation membrane has some unique challenges. For example, the thermodynamic and kinetic factors that control permeation are the preferential solubility of one permeating component over the other and the diffusivity of the permeating components. Since water, as a smaller molecule, has greater diffusivity than polar organic molecules such as 1,3-PD the creation of a pervaporation membrane for polar organic molecules such as 1,3-PD faces significant challenges.

To address the greater diffusivity of water, a high preferential sorption of polar organic molecules and low water solubility in the membrane must be exploited to allow preferential permeation of the polar organic molecule across a membrane. However, the proximity of the thermodynamic solubility parameters of polar organic molecules, such as 1,3-PD, to water and the very hydrophilic character of the polar organic molecules limits the number of appropriate materials useful in pervaporation. These issues can be overcome by finding a solvent for a polar organic molecule and then incorporating the solvent into a repeating unit of a polymer. Preferably the solvent has little or no miscibility with water. This polymer can then be employed in a pervaporation membrane.

Described herein is a polymer having a contact angle with water that is greater than or equal to 90° and a contact angle with an organic molecule that is less than 90° wherein the organic molecule comprises one or more polar functional groups. The polymer can be used in a pervaporation membrane for the separation of the organic molecule from an aqueous mixture. More specifically, the organic molecule is 1,3-PD and the aqueous mixture can be a fermentation broth.

A polymer having a contact angle greater than or equal to 90° with water is hydrophobic. The contact angle may also indicate the relative permeability of the polymer for a specific material. A contact angle greater than or equal to 90° may indicate relatively little permeability of the specific material through the polymer whereas a contact angle less than 90° may indicate relatively greater permeability of the specific material through the polymer.

When the organic molecule is 1,3-PD the solvent incorporated in the polymer can comprise, for example, allylcyclohexylamine or tributyl phosphate. Allylcyclohexylamine can be incorporated into a polymer in several ways. A polysiloxane can be functionalized through reaction with allylcyclohexylamine by hydrosilation using a chloroplatinic acid catalyst solution. This is referred to herein as an allylcyclohexylamine functionalized polysiloxane. The allylcyclohexylamine functionalized polysiloxane can optionally be combined with a polymer such as a styrene-butyl acrylate polymer to form a mixed phase blend. When the allylcyclohexylamine functionalized polysiloxane is combined with a polymer the allylcyclohexylamine functionalized polysiloxane can be present in an amount of 50 to 100 weight percent, or, more specifically, 80 to 100 weight percent, based on the combined weight of the allylcyclohexylamine functionalized polysiloxane and the copolymer.

In another embodiment, the allylcyclohexyl amine can be incorporated into a acrylate monomer such as a methacrylate monomer. For example, the allylcyclohexylamine is coupled with mercaptoethanol and then esterified with methacryloyl chloride to form allylcyclohexylamine functionalized methacrylate monomer. The allylcyclohexylamine functionalized methacrylate monomer can be homopolymerized or copolymerized with vinyl group containing monomers such as butyl acrylate, divinyl benzene, or a combination thereof. When copolymerized the copolymer can comprise 75 to 100 mol %, or, more specifically, 90 to 100 mol % of units derived from the allylcyclohexylamine functionalized methacrylate monomer.

The tributyl phosphate can be incorporated into an acrylate monomer such as a methacrylate monomer by reacting vinylimidazole with mercaptoethanol. The resulting thiolene click adduct can then be reacted with tributyl phosphate to form an ionic liquid with a dibutyl phosphate counter ion. The remaining hydroxyl group on the ionic liquid can then be esterified using methacryloyl chloride and triethyl amine to result in an imidazolium functionalized methacrylate monomer having a dibutyl phosphate counter ion. The methacrylate monomer can then be homopolymerized or copolymerized with a vinyl group containing monomer such as butyl acrylate, divinyl benzene or a combination thereof. When copolymerized the copolymer can comprise 75 to 100 mol %, or, more specifically, 90 to 100 mol % of units derived from the methacrylate ester of the ionic liquid.

The examples using siloxane-based and acrylate, specifically methacrylate-based polymer families indicate this method of tailoring the properties of polymer membranes can be extended to other polymer families such as polyurethanes, polyesters, and others. Generality is indicated because the final separation properties of the membrane are not strongly sensitive to the precise details of the chemistry used to link the polar organic solvent into the polymer structure and the different polymer structures found in siloxanes and acrylates both worked well to produce membranes.

The examples using allylcyclohexylamine and tributyl phosphate, solvents for 1,3-PD, indicate this method of tailoring the properties of polymer membranes can be extended to other solvents for 1,3-PD and to solvents for other polar organic molecules. Generality is indicated because the molecular structures of allylcyclohexylamine and tributyl phosphate are very different from each other, the chemistry details used to link them into the polymers can be quite different, and therefore it is reasonable to expect that many other solvents can be successfully used to form separation membranes.

The applicability of the methods described herein to a wide variety of solvents for polar organic molecules and a wide variety of polymers is illustrated clearly by the examples below. Three examples of novel polymer systems are provided below to illustrate how 1,3-PD may be separated from aqueous mixtures using pervaporation. The three example polymers are based on polysiloxanes and polyacrylates—(i) functionalized siloxane, (ii) allylcyclohexylamine based methacrylate polymers and (iii) vinylimidazolium alkylphosphate ionic liquid based methacrylate polymers. In all three examples, novel monomers are synthesized in which hydrophobic solvents of polar organic molecules have been incorporated. Incorporated means that the solvent has been included in the monomer but might not exist in the monomer in the original molecular form of the solvent. Two examples of hydrophobic solvents were used, allylcyclohexylamine and tributyl phosphate. The allylcyclohexylamine was incorporated into the functionalized silane and into a methacrylate monomer. The tributylphosphate was incorporated into a methacrylate monomer as well. These two examples of hydrophobic solvents exemplify but do not limit the method. The monomers and subsequent polymers, in some cases, contain ionic groups on a substantial fraction of their monomers, including but not limited to imidazolium dibutylphosphate organic salts. The ionic groups are typically present on more than 5% of the monomers, and up to 100% of the monomers.

The polymer can be formed into a pervaporation membrane by several methods known in the art. In an exemplary method a porous polymer sheet such as a polyethylene sheet is soaked in a combination of the polymer and a solvent to result in a membrane. The membranes can then be cured. The membranes can have a thickness of 1 to 1000 micrometers, or, more specifically 300 to 600, micrometers.

The pervaporation membrane can have a mass uptake of water less than 5%, or, more specifically less than 1%. The pervaporation membrane can have a mass uptake of 1,3-PD greater than 2.5%, or, more specifically, greater than 5%. The pervaporation membrane can have a mass uptake of 1,3-PD greater than 15%. In some embodiments the membrane has a mass uptake of 1,3-PD that is less than or equal to 35%. Mass uptake is determined by measuring the initial mass of the polymer and then measuring the mass of the polymer after a period of immersion in a liquid.

The pervaporation membranes can have a mass uptake of ethanol, acetic acid and butyric acid less than or equal to 2%.

The pervaporation membrane can have a separation factor of 1,3-PD relative to water of greater than or equal to 5, or, more specifically, greater than or equal to 7. Separation factor is defined Example 4 and determined by measuring the fluxes of the permeating components.

The pervaporation membrane can have a separation factor of 1,3-PD relative to glycerin of greater than or equal to 1.5, and in some cases, greater than or equal to 2.0

The pervaporation membrane can separate 1,3-PD from a multi-component mixture including water, glycerin, and optionally alcohols and organic acids with separation factors with respect to water that are greater than 2, or, greater than 75. The separation factor can be less than or equal to 100.

The pervaporation membrane can enrich 1,3-PD concentration in a mixture from values of 1-5% to values of 10-50%.

The pervaporation membrane can separate 1,3-PD from aqueous mixtures at a 1,3-PD flux greater than 1 gram/square meter hour (g/m²h), or greater than 3 g/m²h. In some embodiments the 1,3-PD flux is less than 6 g/m²h.

The pervaporation membrane can be used in a pervaporation process. A feed solution comprising the organic molecule such as 1,3-PD is circulated across one surface of the membrane (the upstream side) and the permeate is collected from the opposite surface of the membrane (the downstream side). The feed solution can have a temperature of 15° C. to 50° C., or 15° C. to 40° C. The feed solution can be a fermentation broth. In some embodiments the feed broth is filtered, centrifuged or a combination thereof prior to pervaporation. The permeate is typically collected under conditions of lower temperature and pressure than the conditions of the feed solution. The upstream side can have a gauge pressure of less than 10 atmospheres or less than 2 atmospheres and the downstream side can have an absolute pressure of less than 50 millimeters of Hg, less than 20 millimeters of Hg, or, less than 10 millimeters of Hg. The permeate can be distilled after collection.

This disclosure is further illustrated by the following examples, which are non-limiting.

EXAMPLES

Contact angle measurements were carried out on an Olympus TGHM goniometer. Tensile testing was carried out on rectangular samples of width 10 millimeters (mm) and thickness 200 micrometers on an Instron Universal Testing Machine (UTM). A gauge length of 25.4 mm and a cross head speed of 50 mm/min was employed to obtain break stress and strain values.

Example 1

This example describes a methacrylate polymer comprising repeating units that incorporate functionality derived from tributyl phosphate. Other alkyl phosphates can also be used to generate methacrylate polymers by the same chemical steps illustrated below. Varying the alkyl chain length on the phosphate reactant can be used to tailor the polarity of the resulting polymer to design a family of separation membranes.

Vinylimidazole (VIM), methacryloyl chloride, divinyl benzene (DVB) and butyl acrylate (BuA) were dried prior to use. Mercaptoethanol, tri-ethylamine (TEA) and azobisisobutyronitrile (AIBN) radical initiator were used without modification. The solvents toluene, chloroform, dioxane, and hexane were dried prior to use. All chemicals were purchased from Sigma Aldrich.

The synthesis of the methacrylate monomer is presented in Scheme I.

Methacrylate Monomer      Step 3      Imidazolium Dialkylphosphate Ionic Liquid The thiol-ene adduct was synthesized by AIBN mediated addition of mercaptoethanol to the vinyl double bond of VIM. The reaction was carried out in bulk at 60° C. in the presence of UV light. The reactants were weighed out in nearly stoichiometric amounts with the VIM in slight excess. The product was purified by vacuum removal of excess VIM. The thiol-ene click adduct was characterized by proton NMR and FTIR, while their vaporization temperatures were estimated by TGA. The final yield of the product, gravimetrically measured after driving off the excess VIM was approximately 94%.

A typical run with VIM consisted of 0.01 moles (0.94 g) of vinyl imidazole, 0.01 moles (0.77 g) of mercaptoethanol and 0.02 g of AIBN. The click adduct was subsequently reacted with tributyl phosphate at 140° C. to form the ionic liquid with the dibutyl phosphate anion as the counter ion. The product was characterized by proton NMR. A typical run consisted of 1.7 g of the thiol-ene click adduct and 2.7 g of TBP. The reaction was carried out for at least 72 hours. The remnant hydroxyl group from the mercaptoethanol moiety on the ionic liquid was subsequently esterified using methacryloyl chloride and triethylamine. A typical run consisted of 4.3 g of the ionic liquid, 1 g of triethylamine and 1 g of methacryloyl chloride in approximately 10 milliliters (ml) of solvent. The ionic liquid was dissolved in dry toluene and a stoichiometric amount of methacryloyl chloride and triethylamine were added and refluxed at 75° C. for 12 hours. The solvent was evaporated and the mixture was precipitated in hexane. The triethylamine hydrochloride separated out, and the supernatant hexane layer containing the hydrophobic methacrylate ester of the ionic liquid was filtered off. The hexane was subsequently evaporated and the methacrylate monomer was characterized by proton NMR, carbon 13 NMR, FTIR, and TGA. The absolute density of the methacrylate monomer was measured by weighing a fixed volume of the monomer.

The methacrylate monomer was homopolymerized, and also copolymerized with 5 mol % BuA or 5 mol % DVB using AIBN as initiator. The acronyms used for the homopolymer, butylacrylate copolymer and divinyl benzene copolymer are PVIM, PVIM-BuA and PVIM-DVB, respectively.

Figure 1:
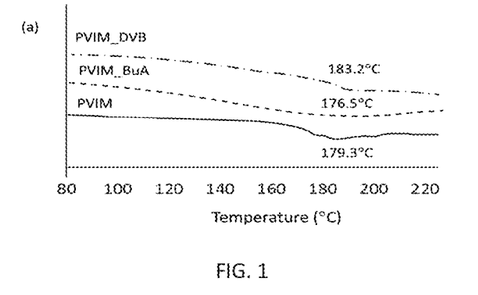
FIG. 1 shows dynamic scanning calorimetry (DSC) of vinyl imidazolium containing acrylate polymers demonstrating the thermal transition temperatures.

The polymerizations were carried out at 70° C. for 4 hours, in a 250 ml two neck round bottom flask fitted with a reflux condenser purged with nitrogen. The dioxane solutions of the monomer(s) were passed through an inhibitor remover column to remove the inhibitor contained in the methacryloyl chloride prior to polymerization. A 25 mL dioxane batch typically consisted of approximately 5 g of the methacrylate monomer with AIBN in a monomer/initiator ratio of 100/1 mass ratio. At the end of each batch, the reaction mixtures were characterized by proton NMR to confirm the formation of the polymer and a portion of the batch was dried by evaporation at 100° C. and then further dried to constant weight at 80° C. under vacuum. The solid polymers were evaluated for thermal transitions by differential scanning calorimetry (DSC). Results are shown in FIG. 1.

The non-crosslinked polymers (i.e. those not employing DVB in their composition) were evaluated by gel permeation chromatography (GPC) for molecular weight. The weight average molecular weight of the homopolymer was 45,073 with a polydispersity index of 4.99 and the weight average molecular weight of the copolymer with butylacrylate was 39,850 with a polydispersity index of 4.06. GPC employed N,N-dimethylacetamide as an eluent and narrow molecular weight poly(methyl methacrylate) as calibration standards.

Example 2

This example describes an allylcyclohexylamine functionalized polysiloxane. Poly(methylhydrosiloxane) (PHMS) having a degree of polymerization of approximately 35 to 40, allylcyclohexylamine (ACA), chloroplatinic acid, dibutyl tin dilaurate, hydroxyl terminated poly(dimethyl siloxane), and tetraethyl orthosilicate (TEOS) were purchased from Sigma Aldrich. The PHMS, ACA, and toluene were dried prior to use.

Porous polyethylene sheets were obtained from Interstate Specialty Products for use as the support sheet for membrane fabrication. The nominal thickness reported was 500 micrometers with pore diameters of 75 to 110 micrometers and a porosity of 48%. Twenty measurements of thickness indicated that the actual thickness was 535±10 micrometers.

A 25 milligram per milliliter (mg/ml) chloroplatinic acid catalyst solution in isopropanol was prepared. The PHMS was functionalized with ACA by hydrosilylation using the chloroplatinic acid catalyst solution. The reaction was carried out in a clean and dry glass pressure tube flushed with high purity argon on a Schlenk line. A typical run consisted of 1.5 g PHMS with varying quantities of ACA, depending upon the targeted extent of substitution, and 1 ml of toluene as solvent. The catalyst solution was added in an amount of 5 microliter per milliliter (μl/ml) of reaction volume. The reaction temperature was controlled at 70±2° C. All reagents were thoroughly dried prior to use.

Figure 2:
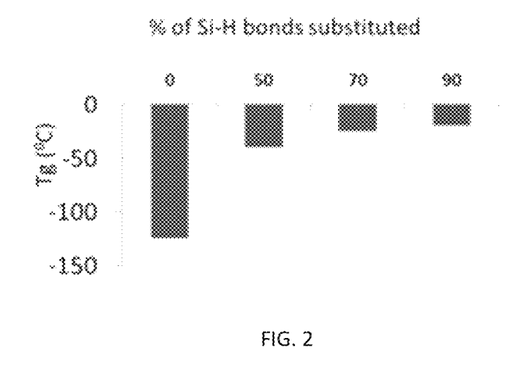
FIG. 2 shows dynamic scanning calorimetry (DSC) of allylcyclohexylamine containing PHMS polymers demonstrating the thermal transition temperatures.
Figure 3:
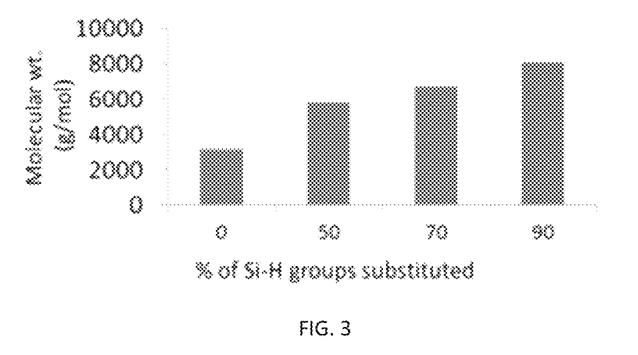
FIG. 3 shows gel permeation chromatography (GPC) results of allylcyclohexylamine containing PHMS polymers showing the molecular weight.

The reaction was monitored by proton NMR and FTIR. When the reaction was complete the polymer solution was cooled by immersing the pressure tube in a cry ice and acetone mixture, with a small amount of liquid nitrogen, to facilitate the separation of the functionalized polymer from the solvent, remaining catalyst, and unreacted volatiles. The functionalized PHMS was re-dissolved in toluene, the procedure repeated thrice and the remnant toluene solvent removed by evaporation. The polymer was washed with ethanol and vacuum dried. The functionalized polymer was characterized for glass transition temperature by DSC (results are shown in FIG. 2) and weight average molecular weight by GPC as shown in FIG. 3. The ACA functionalized polymers retained flow even at 90% substitution level, indicating that there was no hydride elimination and hence no significant crosslinking during the reaction. The increase in molecular weight observed by GPC was quantitatively corroborated by nuclear magnetic resonance observations of increasing levels of substitution of Si—H bonds.

The ACA functionalized PHMS was blended with the high molecular weight silanol terminated polydimethylsiloxane (HPDMS) and TEOS. The HPDMS and TEOS were kept at 10% and 2% of the total weight of the mixture respectively. Undiluted dibutyl tin dilaurate catalyst was added to this mixture at 0.1% by weight of the mixture. A small amount of toluene was added to lower the viscosity.

Figure 4:
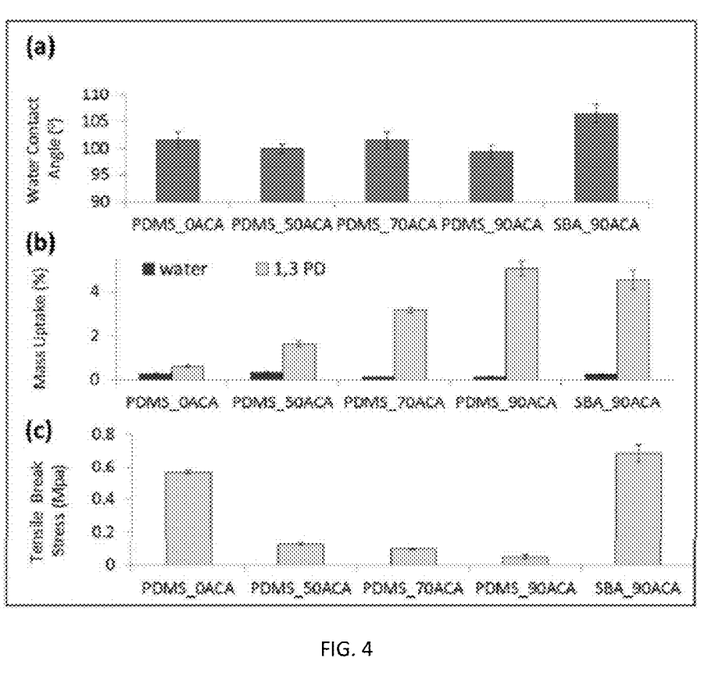
FIG. 4 shows water contact angle (a), mass uptake (b), and tensile break stresses (c) of allylcyclohexylamine containing PHMS polymers.

The blends were cast as thin layers on clean glass slides for water contact angle measurements. The water contact angles varied from 99.5° to 106°. Blends were fabricated using 50 mole %, 70 mole % and 90 mole % ACA functionalized PHMS and were given the nomenclature PDMS_50ACA, PDMS_70ACA, and PDMS_90ACA respectively. Results are shown in FIG. 4. The blends were also tested for mass uptake of water and 1,3-PD and their tensile strength was measured. The blends were separately cast on a Kapton sheet into 100 micron thick sheets for tensile tests. Pieces of these sheets were used for mass uptake experiments and DSC measurements. Mass uptake results are shown in FIG. 4b, indicating that the polymers became more hydrophobic as the ACA content increased (water mass uptake decreased slightly) and the polymers became much more 1,3-PD philic as the ACA content increased (1,3-PD mass uptake increased from roughly ½% to roughly 5%). Tensile testing results are also shown in FIG. 4c. As the ACA content increased from 0 (PDMS_0ACA) to 90% (PDMS_90ACA), the tensile strength decreased greatly from over 0.5 MPa to less than 0.1 MPa. The larger value labeled SBA_90ACA is discussed in the next example.

A piece of porous polyethylene sheet was soaked in measured quantities of the blends and the solvent was allowed to evaporate at room temperature over a period of approximately 24 hours. The membrane was then allowed to cure at 60° C. for 4 days to ensure completion of crosslinking and then cut into the required shape. Membranes were fabricated using 50 mole %, 70 mole % and 90 mole % ACA functionalized PHMS and were given the nomenclature PDMS_50ACA, PDMS_70ACA, and PDMS_90ACA respectively. The membranes had a thickness of 643±20 micrometers. The thickness includes a top layer of polymer having a thickness of 108±16 micrometers.

Pervaporation was carried out in a membrane holder having a pervaporation area of 43 square centimeters. Feed solutions consisting of 1,3-propane diol and water were maintained at various temperatures. The feed solutions were recirculated over the membranes on a perforated brass support in the membrane holder by a peristaltic pump, providing various cross flow rates. The permeate was collected in two parallel cold traps cooled in a dry ice-acetone bath. A vacuum pump was employed to maintain the permeate side pressure at less than 1 mm Hg. Permeate samples were collected a regular time intervals until steady state was reached. The permeate compositions were analyzed by gas chromatography.

Figure 5:
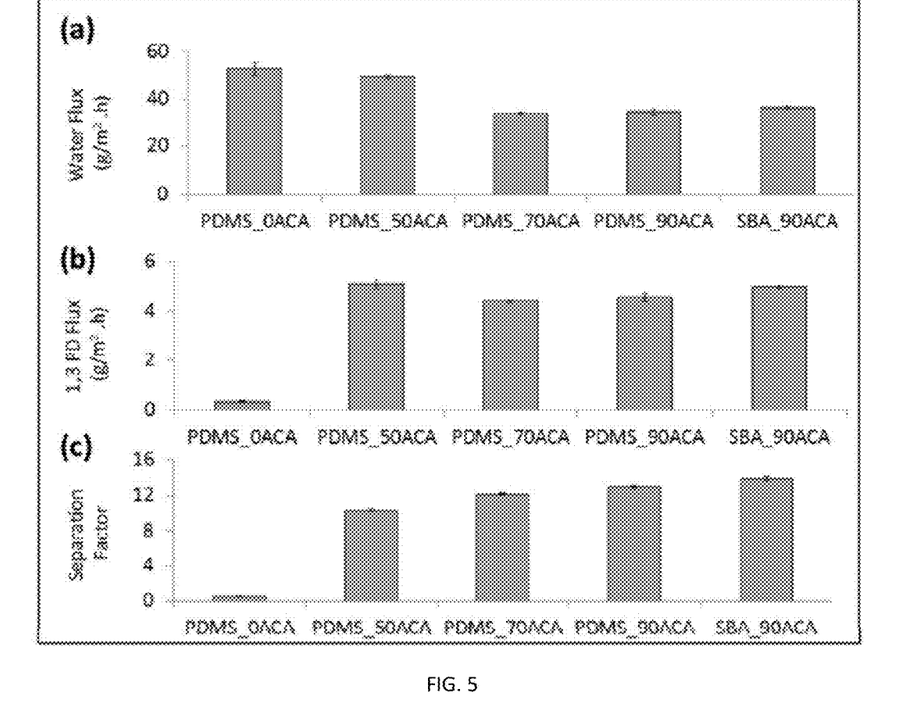
FIG. 5 shows steady state water flux (a), 1,3-PD flux (b), and separation factor (c) during pervaporation of binary water/1,3-PD solutions through allylcyclohexylamine containing PHMS polymer membranes.

FIG. 5 illustrates the variation of steady-state component fluxes and separation factors with increasing allylcyclohexylamine functionalization. Separation factors of 1,3-PD relative to water were achieved in excess of 12 for the PDMS_90ACA membrane. The effectiveness of ACA functionalization is clearly apparent by comparing these results with the data of the PDMS_0ACA, where no ACA was reacted into the siloxane network.

Example 3

The allylcyclohexylamine functionalized polysiloxane of Example 2 (90 mole % ACA functionalized PHMS) was combined with a styrene-butyl acrylate copolymer. Styrene and butyl acrylate were purchased from Sigma Aldrich and passed through a column of inhibitor remover prior to emulsion polymerization. Potassium persulfate, tert-butyl perbenzoate, sodium bicarbonate, and sodium dodecylbenzenesulfonate were obtained from Sigma Aldrich and used without modification.

A high molecular weight styrene-butyl acrylate copolymer (SBA) was synthesized by emulsion polymerization. The reaction was carried out at 80° C. in a 250 ml two necked round bottom flask fitted with a reflux condenser with the system being constantly purged with nitrogen. A typical batch consisted of 50 g deionized water, 0.5 g potassium persulfate, 0.25 g sodium bicarbonate, 1 g sodium dodecylbenzenesulfonate 0.25 g tert-butyl perbenzoate, 50 g butyl acrylate and 50 g styrene. Sodium bicarbonate and sodium dodecylbenzenesulfonate were added beforehand and the monomer mixture was added dropwise over a period of 15 minutes through the second neck. After the monomer addition, the temperature was reduced to 65° C. and the potassium persulfate and tert-butyl perbenzoate added and the reaction was allowed to run for 2 hours. A silicone rubber tube fitted with a needle was used to blanket the surface of the reaction mixture with nitrogen throughout the 2 hour course of the reaction. At the end of the reaction, the emulsion was flocculated by sodium chloride, the flocculated polymer washed thoroughly and repeatedly, centrifuged and dried at room temperature.

90 mole % ACA functionalized PHMS was blended with the emulsion polymerized styrene-butylacrylate polymer (SBA) and TEOS. The SBA and TEOS were kept at 10% and 2% of the total weight while the dibutyl tin dilaurate catalyst was kept at 0.1% by weight of the mixture. A small amount of toluene was added to this mixture to lower its viscosity. The blend was tested for contact angles, mass uptake, and tensile strength as described above with regard to Example 2. Results are shown in FIG. 4 and designated SBA_90ACA. Importantly, this blend of functionalized PHMS with SBA has much greater tensile strength than the blend of functionalized PHMS with HPDMS (previous example). The separation performance of this blend was also tested in pervaporation and the results are shown in FIG. 5. Most importantly, this blend with SBA resulted in very similar separation performance as the blend with HPDMS (previous example), illustrating the possibility of optimizing the combined mechanical and separation performance of these membranes.

Example 4

This example describes a methacrylate polymer comprising repeating units that incorporate functionality derived from allylcyclohexylamine. Allylcyclohexylamine, toluene, chloroform, dioxane, hexane, methacryloyl chloride, divinyl benzene, and butyl acrylate were dried prior to use. Mercaptoethanol, AIBN, and trimethylamine were used without modification. All reagents and solvents were purchased from Sigma Aldrich.

The monomer synthesis scheme is depicted in Scheme II.

(II)

The thiol-ene click chemistry adduct was synthesized by AIBN mediated addition of mercaptoethanol to the allyl double bond of the ACA. The reaction was carried out in a pressure tube, in bulk, and in the presence of UV light at 60° C. The pressure tube was degassed with dry argon in a Schlenk line and the reactants were kept under argon. The reactants were weighed out in nearly stoichiometric amount, with the ACA being in slight excess. The progress of the reaction was checked after 24 hours by proton NMR. The product was purified by vacuum removal of the excess ACA, which is the lower boiling component. The purified click adduct was characterized by FTIR and NMR, and its vaporization temperature was estimated by TGA. A typical run consisted of 0.01 moles (~1.4 g) of ACA with 0.01 moles (~0.77 g) of mercaptoethanol, mixed together in a Schleck tube with ~0.0002 moles (0.033 g) of AIBN. The final yield of the product, gravimetrically measured, after driving off the excess ACA was approximately 94%.

The click adduct was esterified using methacryloyl chloride and triethylamine as the catalyst to form the methacrylate monomer. The click adduct was dissolved in dry toluene and a stoichiometric amount of methacryloyl chloride and triethylamine were added, and the mixture was refluxed at 70° C. for 12 hours. The toluene was evaporated from the system at 40° C. overnight. The resultant mixture of the methacrylate monomer and triethylamine hydrochloride was added to hexane. The triethylamine hydrochloride being hexane insoluble separated, and the supernatant fluid containing the methacrylate monomer was filtered and the hexane evaporated overnight in a vacuum oven at 40° C. In a typical run 0.0092 moles (2 g of the click adduct) was reacted with an equimolar amount of methacryloyl chloride (0.0092 moles, 0.96 g) using an equimolar amount of triethylamine as catalyst (0.94 g) in 7 ml of dry toluene as solvent for the reaction.

Figure 6:
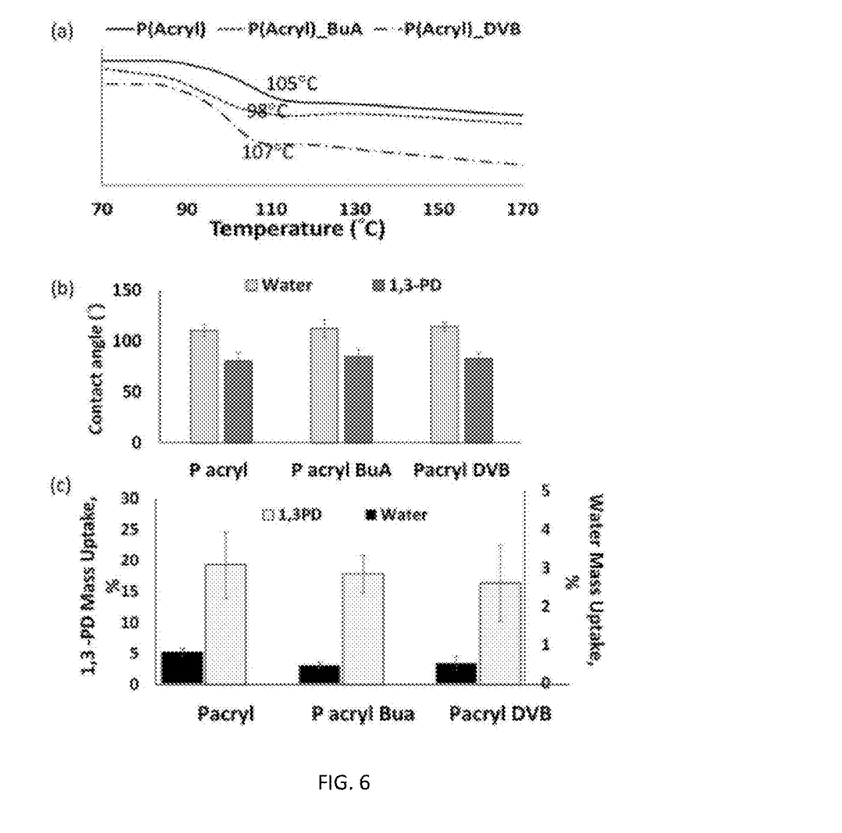
FIG. 6 shows characterization of allylcyclohexylamine containing acrylate polymers: (a) Dynamic scanning calorimetry (DSC) showing thermal transitions, (b) contact angle with water and with 1,3-PD, and (c) mass uptake of water and of 1,3-PD.

The homopolymerization of the synthesized methacrylate monomer and its copolymerizations with 5 mol % BuA or 5 mol % DVB were initiated by AIBN in dioxane at 70° C. in a 250 ml two necked round bottom flask fitted with a reflux condenser with the system being constantly purged with nitrogen. The resultant polymers are referred to below as P(Acryl), P(Acryl)_BuA and P(Acryl)_DVB, respectively. Prior to polymerization, the dioxane solutions of the monomer(s) were passed through an inhibitor removal column. For a typical run, a 25 mL dioxane batch contained 5 g of the methacrylate monomer. The stoichiometric molar ratio of the methacrylate monomer to AIBN was kept at 100:1 in all batches. A silicone rubber tube fitted with a needle was used to blanket the surface of the reaction mixture with nitrogen throughout the 4-hour course of each polymerization. At the end of each polymerization, a portion of the batch was dried by evaporation at 100° C. and then further dried to constant weight at 80° C. under vacuum. The thermal transitions of the solid polymers were estimated by DSC. The reaction mixtures were used to cast films of the polymers and copolymers on clean glass substrates for evaluation of the contact angle. Films were similarly cast on a Kapton surface and peeled off for evaluation of solvent uptake. The results for water and 1,3-PD contact angles, mass uptake and DSC thermal transitions are shown in FIG. 6. The non-crosslinked polymers (i.e. those not employing DVB in their composition) were evaluated by GPC.

Figure 7:
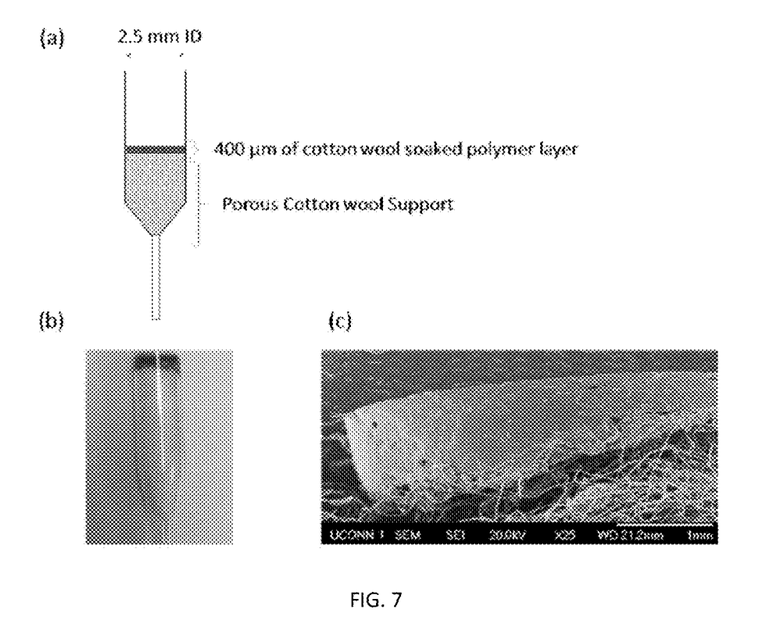
FIG. 7 shows construction of plug membrane system for batch pervaporation experiments with allylcyclohexylamine containing acrylate polymer membranes: (a) schematic diagram, (b) photograph, and (c) electron micrograph of membrane.

Plug membranes were fabricated inside 2.5 mm inner diameter glass pipettes. The glass pipettes were weighed and stuffed with a known weight of dry cotton wool. A small, but known weight of dry cotton wool was separately soaked with the polymer solution and the solvent allowed to evaporate slowly at 40° C. over a period of 3-4 days. When the solvent had nearly all evaporated, the polymer solution soaked cotton wool was lightly pressed with a flat surface to set the membrane on top of the cotton wool base inside the glass pipettes, and the weight of the plug noted. The solvent was allowed to further evaporate over a period of 1 week at room temperature till the plug attained a constant weight. The slow solvent evaporation was carried out to prevent the formation of pinholes and to allow the plug membrane to adhere to the inner wall of the glass pipettes. This process gave rise to a fiber supported membrane structure. The volume inside the glass pipette above the membrane was used to hold ~1.5-1.7 ml of pervaporation feed solution. Plug membrane structures are schematically depicted in FIG. 7(a) along with a picture of the actual membrane plug in FIG. 7(b). FIG. 7(c) is an FESEM image of the membrane.

Batch pervaporation experiments were carried out on the fabricated plug membranes. The plug membrane structures were affixed in an upright position in a water bath maintained at 30° C., 40° C., or 50° C. The membranes were monitored for leakage by checking for abnormally high flux. The plug membranes had a pervaporation area of 4.91 mm².

Figure 8:
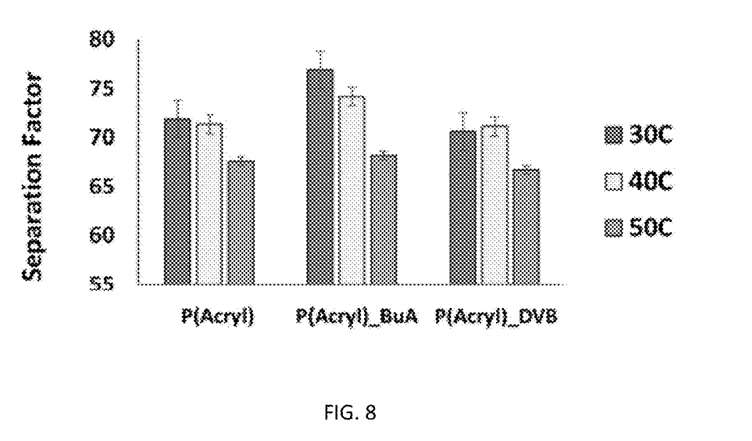
FIG. 8 shows separation factor results for batch pervaporation experiments with allylcyclohexylamine containing acrylate polymer membranes using a binary mixture of 1 mass % 1,3-PD dissolved in water.
Figure 9:
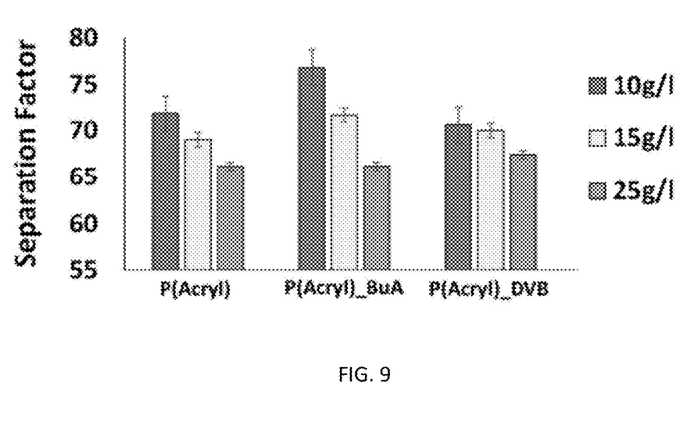
FIG. 9 shows separation factor results for batch pervaporation experiments with allylcyclohexylamine containing acrylate polymer membranes at three different concentrations of 1,3-PD in water.

Each batch pervaporation experiment was allowed to run for a period of 20 hours. The permeate was collected in a cold trap, cooled in a dry ice-acetone bath. A vacuum pump was employed to maintain the permeate side pressure at less than 1 mm Hg. The permeate collected was weighed and analyzed for 1,3-PD concentration by gas chromatography. The key performance indicators of the pervaporation experiment were defined by the component fluxes and the separation factor defined as:

$$\alpha = \frac{Jp}{Jw} \cdot \frac{xw}{xp}$$

where Jp and Jw represent the 1,3-PD and water fluxes and xp and xw represent the initial feed mass fractions of 1,3-PD and water, respectively. The respective fluxes of water and 1,3-PD and the separation factor of 1,3-PD over water were computed. Batch pervaporation experiments do not achieve a true steady state. In these experiments the total permeation of water and 1,3-PD changed the feed composition by less than 5% over the course of the entire pervaporation experiment. The polymers demonstrate separation factors in the range 65 to 80. The 1,3-PD fluxes vary between 1.9 g/m$^2$h and 3.4 g/m$^2$h, while the water fluxes range between 3.5 g/m$^2$h to 5 g/m$^2$h. Results are shown in FIG. 8. The effect of feed concentration was also examined. Results are shown in FIG. 9.

Example 5

The pervaporative performance of the membranes of Examples 2 and 4 with binary 1,3-PD/water feed solutions was compared to the performance of the same membranes with model broth solutions. The model broth solutions have varying concentrations of a range of metabolites as shown below:
  Feed composition M1: 1,3-PD: 10 g/l, Glycerol: 15 g/l, Acetic Acid: 1.5 g/l, Butyric acid: 2 g/l, Ethanol: 0.5 g/l
  Feed composition M2: 1,3-PD: 6 g/l, Glycerol: 25 g/l, Acetic Acid: 1 g/l, Butyric acid: 1.5 g/l, Ethanol: 0.2 g/l
  Feed composition M3: 1,3-PD: 3 g/l, Glycerol: 30 g/l, Acetic Acid: 0.5 g/l, Butyric acid: 0.5 g/l, Ethanol: 0.1 g/l A quantitative estimation of the coupling effect was studied by comparing the overall mass transfer coefficients obtained in the binary feed experiments to those obtained with model broth feeds under corresponding and comparable experimental conditions.

Figure 10:
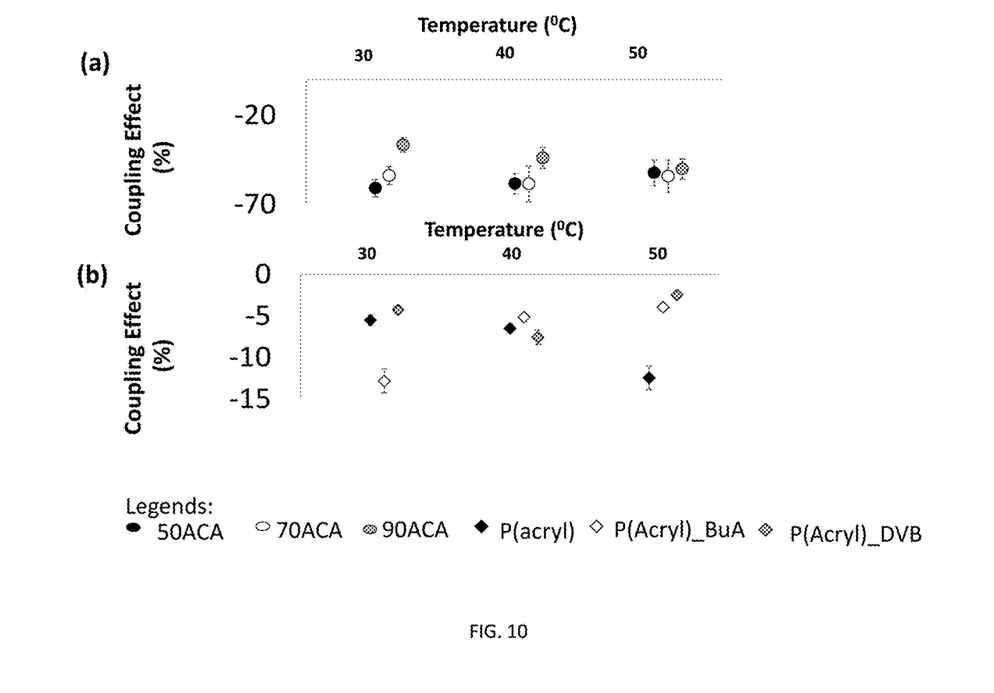
FIG. 10 shows a comparison of separation using model fermentation broth to separation using binary water/1,3-PD solutions by the coupling effect formalism for (a) allylcyclohexylamine containing PHMS polymer membranes and (b) allylcyclohexylamine containing acrylate polymer membranes.

The coupling effect was estimated quantitatively by the following equation:

$$CE(\%) = \left( \frac{K''_{PD} - K'_{PD}}{K'_{PD}} \right) \times 100$$

where CE (%) is the coupling effect, $K''_{PD}$, and $K'_{PD}$ are the overall mass transfer coefficients of 1,3-PD for the separation from the binary feed solutions versus model broth compositions, respectively. It is to be noted that the mass transfer coefficients for binary and model solutions used for comparison pertained to comparable experimental conditions. For example, membrane system, the feed temperature, feed 1,3-PD concentration and cross flow rate, wherever applicable, were the same for the data sets used for computation. The computed coupling effects versus temperature are graphically shown in FIG. 10. Both polymers show a negative coupling effect, which means the presence of glycerol and other components in the feed mixture adversely affect the 1,3-PD flux, a fact that is seen in the slight reduction in separation factors compared to binary feeds.

The coupling effect is distinctly higher for the siloxane polymers with multicomponent feed pervaporation versus binary feeds. The coupling effect appears to be greater for lower levels of functionalization than at 30° C. As the temperature increases to 50° C., the coupling effect levels out for all siloxane polymers studied. For the 50 ACA polymer the coupling effect decreases with temperature while for the 90ACA polymer the opposite effect is seen.

The P(Acryl) homopolymer showed a small increase in the coupling effect with increase in temperature, perhaps due to enhanced glycerol dissolution in the membrane with temperature which adversely affected both the 1,3-PD flux as well as enrich over water and glycerol. No particular trend with temperature could be ascertained for the butyl acrylate copolymer. There was a minimal temperature effect on the CE % with the P(Acryl)_DVB copolymer.

This disclosure further encompasses the following embodiments.

Embodiment 1

A polymer having a contact angle with water that is greater than or equal to 90° and a contact angle with 1,3-propane diol that is less than 90°.

Embodiment 2

The polymer of Embodiment 1, wherein the polymer comprises repeating united derived from allylcyclohexylamine or tributyl phosphate.

Embodiment 3

The polymer of Embodiment 2, wherein the polymer comprises allylcyclohexylamine functionalized polysiloxane.

Embodiment 4

The polymer of Embodiment 2, wherein the polymer comprises a repeating unit derived from an allylcyclohexylamine based acrylate, specifically a methacrylate.

Embodiment 5

The polymer of Embodiment 2, wherein the polymer comprises a repeating unit derived from an imidazolium functionalized acrylate monomer, specifically a methacrylate monomer having a dibutyl phosphate counter ion.

Embodiment 6

A pervaporation membrane comprising a polymer having a contact angle with water that is greater than or equal to 90° and a contact angle with 1,3-propane diol that is less than 90°.

Embodiment 7

The pervaporation membrane of Embodiment 6, wherein the polymer comprises repeating units derived from allylcyclohexylamine or tributyl phosphate.

Embodiment 8

The pervaporation membrane of Embodiment 7, wherein the polymer comprises allylcyclohexylamine functionalized polysiloxane.

Embodiment 9

The pervaporation membrane of Embodiment 8, wherein the membrane further comprises styrene-butyl acrylate copolymer.

Embodiment 10

The pervaporation membrane of Embodiment 7, wherein the polymer comprises a repeating unit derived from an allylcyclohexylamine based methacrylate.

Embodiment 11

The pervaporation membrane of Embodiment 7, wherein the polymer comprises a repeating unit derived from an imidazolium functionalized acrylate monomer, specifically a methacrylate monomer having a dibutyl phosphate counter ion.

Embodiment 12

The pervaporation membrane of any of Embodiments 5 to 11, wherein the membrane has a separation factor of 1,3-propane diol relative to water of greater than or equal to 5.

Embodiment 13

The pervaporation membrane of any of Embodiments 5 to 12, wherein the membrane has a separation factor of 1,3-propane diol relative to glycerin greater than or equal to 1.5.

Embodiment 14

The process for purifying a fermentation broth comprising: contacting the broth with a pervaporation membrane under pervaporation conditions to produce a product comprising 1,3-propane diol wherein the pervaporation membrane comprises a polymer having a contact angle with water that is greater than or equal to 90° and a contact angle with 1,3-propane diol that is less than 90° and the fermentation broth comprises 1,3 propane diol.

Embodiment 15

The process of Embodiment 14, further comprising removing solids from the fermentation broth prior to contact with the pervaporation membrane.

Embodiment 16

The process of Embodiment 14 or 15, further comprising distilling the product comprising 1,3-propane diol.

Embodiment 17

The process of any of Embodiments 14 to 16, wherein the pervaporation membrane has an upstream side and a downstream side and a gauge pressure on the upstream side is less than 10 atmospheres and absolute pressure on the downstream side is less than 50 millimeters of Hg.

Embodiment 18

The process of any of Embodiments 14 to 17, wherein the temperature of the fermentation broth is 15 to 50° C.

Embodiment 19

The process of any of Embodiments 14 to 18, wherein the pervaporation membrane has a mass uptake of water less than 1% and a mass uptake of 1,3 propane diol greater than 2.5%.

Embodiment 20

The process of any of Embodiments 14 to 19, wherein the pervaporation membrane has a separation factor of 1,3-propane diol relative to water greater than or equal to 5.

Embodiment 21

The process of any of Embodiments 14 to 20, wherein the polymer comprises repeating units derived from allylcyclohexylamine or tributyl phosphate.

Embodiment 22

The process of any of Embodiments 14 to 21, wherein the polymer comprises allylcyclohexylamine functionalized polysiloxane.

Embodiment 23

The process of any of Embodiments 14 to 22, wherein the membrane further comprises styrene-butyl acrylate copolymer.

Embodiment 24

The process of any of Embodiments 14 to 21, wherein the polymer comprises a repeating unit derived from an allylcyclohexylamine based acrylate, specifically a methacrylate.

Embodiment 25

The process of Embodiment 21, wherein the polymer comprises a repeating unit derived from an imidazolium functionalized acrylate, specifically a methacrylate monomer having a dibutyl phosphate counter ion.

Embodiment 26

A process of purifying biologically-produced 1,3-propanediol from the fermentation broth of an organism able to produce 1,3-propanediol, comprising: performing pervaporation using polymer membranes designed to selectively pass 1,3-propanediol through the membrane while rejecting water and most other materials.

The compositions, methods, and articles can alternatively comprise, consist of, or consist essentially of, any appropriate components or steps herein disclosed. The compositions, methods, and articles can additionally, or alternatively, be formulated so as to be devoid, or substantially free, of any steps, components, materials, ingredients, adjuvants, or species that are otherwise not necessary to the achievement of the function or objectives of the compositions, methods, and articles.

All ranges disclosed herein are inclusive of the endpoints, and the endpoints are independently combinable with each other (e.g., ranges of "up to 25 wt. %, or, more specifically, 5 wt. % to 20 wt. %", is inclusive of the endpoints and all intermediate values of the ranges of "5 wt. % to 25 wt. %," etc.). "Combinations" is inclusive of blends, mixtures, alloys, reaction products, and the like. The terms "first," "second," and the like, do not denote any order, quantity, or importance, but rather are used to distinguish one element from another. The terms "a" and "an" and "the" do not denote a limitation of quantity, and are to be construed to cover both the singular and the plural, unless otherwise indicated herein or clearly contradicted by context. "Or" means "and/or" unless clearly stated otherwise. Reference throughout the specification to "some embodiments", "an embodiment", and so forth, means that a particular element described in connection with the embodiment is included in at least one embodiment described herein, and may or may not be present in other embodiments. In addition, it is to be understood that the described elements may be combined in any suitable manner in the various embodiments.

Unless defined otherwise, technical and scientific terms used herein have the same meaning as is commonly understood by one of skill in the art to which this application belongs. All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A pervaporation membrane comprising a polymer having a contact angle with water that is greater than or equal to 90° and a contact angle with 1,3-propane diol that is less than 90° wherein the polymer comprises allylcyclohexylamine functionalized polysiloxane or repeating units derived from an allylcyclohexylamine based acrylate.

2. The pervaporation membrane of claim 1, wherein the polymer comprises allylcyclohexylamine functionalized polysiloxane and the membrane further comprises styrene-butyl acrylate copolymer.

3. The pervaporation membrane of claim 1, wherein the polymer comprises a repeating unit derived from an imidazolium functionalized acrylate monomer having a dibutyl phosphate counter ion.

4. The pervaporation membrane of claim 1, wherein the membrane has a separation factor of 1,3-propane diol relative to water of greater than or equal to 5.

5. The pervaporation membrane of claim 4, wherein the membrane has a separation factor of 1,3-propane diol relative to glycerin greater than or equal to 1.5.

6. The process for purifying a fermentation broth comprising:
contacting the broth with the pervaporation membrane of claim 1 pervaporation conditions to produce a product comprising 1,3-propane diol wherein the pervaporation membrane comprises a polymer having a contact angle with water that is greater than or equal to 90° and a contact angle with 1,3-propane diol that is less than 90° and the fermentation broth comprises 1,3-propane diol.

7. The process of claim 6, further comprising removing solids from the fermentation broth prior to contact with the pervaporation membrane.

8. The process of claim 6, further comprising distilling the product comprising 1,3-propane diol.

9. The process of claim 6, wherein the pervaporation membrane has an upstream side and a downstream side and a gauge pressure on the upstream side is less than 10 atmospheres and absolute pressure on the downstream side is less than 50 millimeters of Hg.

10. The process of claim 6, wherein the temperature of the fermentation broth is 15 to 50° C.

11. The process of claim 6, wherein the pervaporation membrane has a mass uptake of pure water less than 1% and a mass uptake of pure 1,3-propane diol greater than 2.5%.

12. The process of claim 6, wherein the pervaporation membrane has a separation factor of 1,3-propane diol relative to water greater than or equal to 5.

13. The process of claim 6, wherein the polymer comprises repeating units derived from allylcyclohexylamine or tributyl phosphate.

14. The process of claim 13, wherein the polymer comprises allylcyclohexylamine functionalized polysiloxane.

15. The process of claim 14, wherein the membrane further comprises a styrene-butyl acrylate copolymer.

16. The process of claim 13, wherein the polymer comprises a repeating unit derived from an allylcyclohexylamine based acrylate.

17. The process of claim 13, wherein the polymer comprises a repeating unit derived from an imidazolium functionalized acrylate monomer having a dibutyl phosphate counter ion.

* * * * *